United States Patent [19]

Astegger et al.

[11] Patent Number: 5,118,423
[45] Date of Patent: Jun. 2, 1992

[54] METHOD OF REMOVING WATER FROM A DILUTE SOLUTION OF N-METHYLMORPHOLINE-N-OXIDE, N-METHYLMORPHOLINE, OR MORPHOLINE

[75] Inventors: Stephan Astegger; Dieter Eichinger; Heinrich Firgo, all of Vöcklabruck; Karin Weinzierl, Timelkam; Bernd Wolschner, Vöcklabruck; Stefan Zikeli, Regau, all of Austria

[73] Assignee: Lenzing Aktiengesellschaft, Lenzing, Austria

[21] Appl. No.: 675,565

[22] Filed: Mar. 27, 1991

[30] Foreign Application Priority Data

Mar. 28, 1990 [AT] Austria .................................. 722/90

[51] Int. Cl.$^5$ ............................................. B01D 61/02
[52] U.S. Cl. ..................................... 210/638; 210/652
[58] Field of Search ............... 210/651, 652, 653, 654, 210/500.23, 638

[56] References Cited

U.S. PATENT DOCUMENTS

| 1,144,048 | 6/1915 | Muller | 49/223 |
| 3,228,877 | 1/1966 | Mahon | 210/500.23 X |
| 4,748,241 | 5/1988 | Scholten et al. | 544/173 |
| 4,944,882 | 7/1990 | Ray et al. | 210/641 X |

Primary Examiner—Frank Spear
Attorney, Agent, or Firm—Herbert Dubno; Jonathan Myers

[57] ABSTRACT

For the removal of water from dilute aqueous solution of NMMO, N-methylmorpholine or morpholine or mixtures thereof, the solution is subjected to reverse osmosis at a pressure in excess of the osmotic pressure and probably around 40 bar and a temperature of 25° C. to 75° C. to form a retentate containing the amines and a permeate which is practically free from the amines. The permeate can be used as process water while the retentate can be worked up to NMMO for reuse in the cellulose solubilization process.

4 Claims, 1 Drawing Sheet

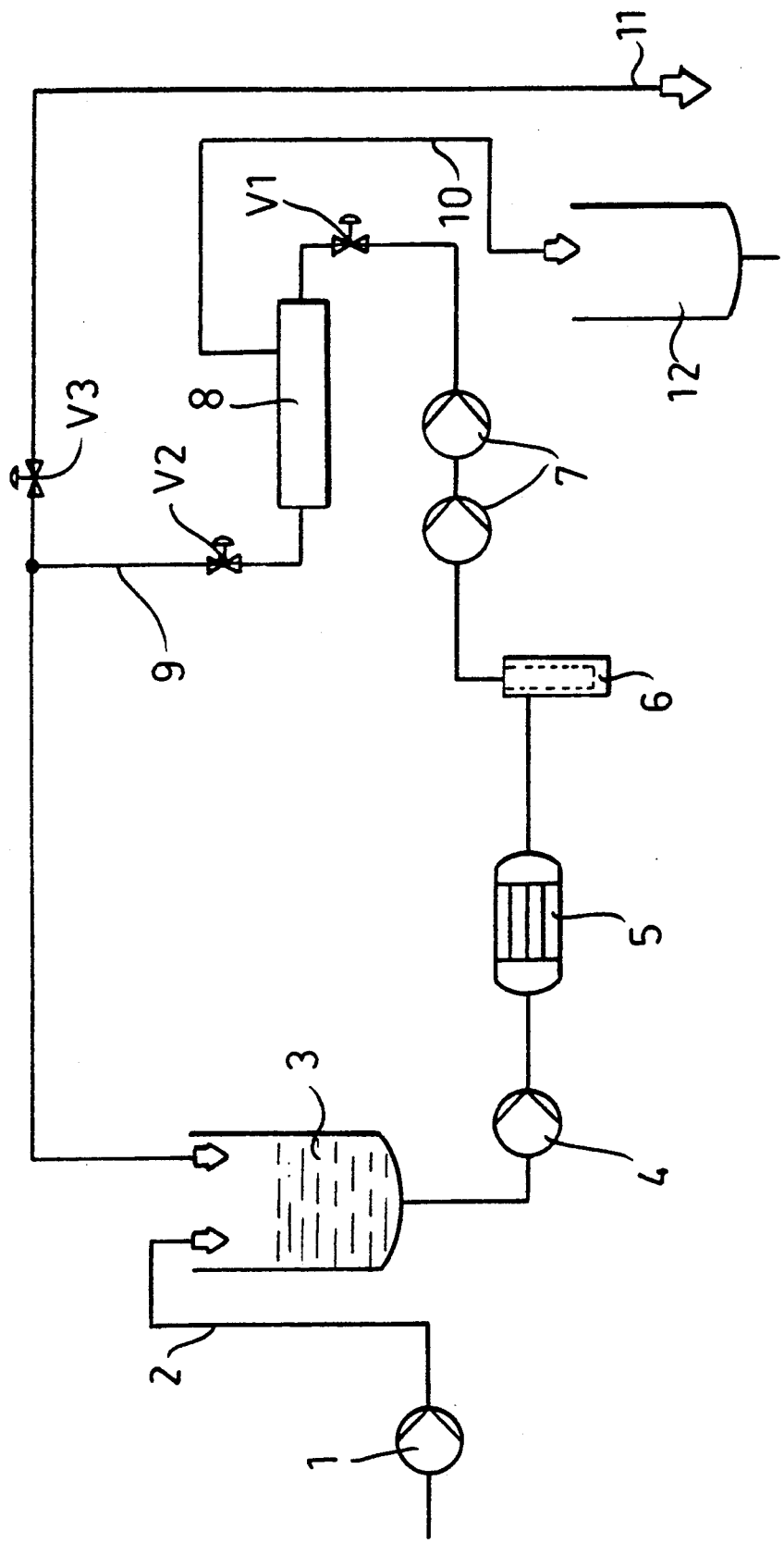

METHOD OF REMOVING WATER FROM A DILUTE SOLUTION OF N-METHYLMORPHOLINE-N-OXIDE, N-METHYLMORPHOLINE, OR MORPHOLINE

FIELD OF THE INVENTION

Our present invention relates to a method of removing water from a dilute aqueous solution of N-methylmorpholine-N-oxide, N-methylmorpholine, morpholine or mixtures thereof obtained or produced in the production of cellulose products or solutions utilized in the processing of yarns. More specifically, the invention relates to a method of concentrating dilute aqueous solutions of N-methyl-morpholine-N-oxide, N-methylmorpholine or morpholine or mixtures thereof.

BACKGROUND OF THE INVENTION

In the production of articles from cellulose, cellulose may have to be dissolved to form a solution thereof. The dissolution of cellulose can be effected with a solvent which is a mixture of N-methyl-morpholine-N-oxide (hereinafter NMMO) and water. The dissolved cellulose can be extruded or spun and thereafter precipitated with the aid of water to yield a film, thread or filament or a shaped body or material having a cellulose base (see Austrian Patent 376 986).

To dissolve the cellulose, a mixture of cellulose, water and NMMO is agitated under vacuum and heated water is drawn off until the cellulose has been completely solubilized. The resulting water vapor is condensed in a condenser. As a result of the thermal action on the NMMO, dependent upon the temperature and the duration of the thermal loading, the cellulose concentration and the quality of NMMO used, N-methylmorpholine and morpholine can be formed. Both of these substances are volatile and are condensed with the water vapor in the head product (so-called vapor condensate). The latter may also include spattering or spray from the original NMMO solution, and a delay in boiling can also entrain NMMO into the vapor condensate.

The vapor condensate which is thus obtained can include a maximum of 5% N-methylmorpholine, morpholine and NMMO. The vapor condensate is an environmental pollutant and cannot be discharged without treatment. It also represents a loss of valuable chemicals with respect to the morpholine, N-methylmorpholine and NMMO.

It is, therefore, necessary to treat the vapor condensate to remove the N-methylmorpholine, morpholine and NMMO therefrom or, conversely, to recover them from the water of the vapor condensate. This cannot be done easily or at sufficiently low cost by distillation or rectification. A separation utilizing cation exchange resins can be used but, after the ion exchange material has been loaded, it must be regenerated with inorganic or organic acids. This entails a number of drawbacks.

The use of inorganic or organic acids for regeneration gives rise to significant waste water loading with the regenerating acids and any rinsing liquids which may be required. The regeneration with organic acids permits a recirculation of the regenerating acid and complete disposal by combustion. However, the removed amines cannot be recycled or reprocessed since they are recovered as salts which pose problems in processing and, particularly, results in chemical losses. The capital cost and operating cost of apparatus of the ion exchange process are relatively high.

OBJECTS OF THE INVENTION

It is, therefore, the principal object of the present invention to provide an improved method of recovering N-methylmorpholine, morpholine and NMMO mixtures thereof from aqueous solutions.

Another object of the invention is to provide a method of treating vapor condensates of the type described to concentrate the amines without the drawbacks of the systems previously described.

The precipitating bath in which the cellulose is precipitated in the NMMO process does, of course, eventually contain NMMO and it is desirable to be able to reuse this NMMO for the dissolution of additional cellulose. As a consequence the NMMO in the precipitating bath must be concentrated. If this is to be achieved by distillation, a portion of the NMMO is converted to the N-methylmorpholine and morpholine so that there is a need for an alternative to distillation. It is, therefore, another object of the invention to provide an improved method of concentrating very dilute solutions of NMMO, N-methylmorpholine, morpholine and mixtures thereof obtained in that manner.

It has also been found that solutions of all kinds used in the treatment of yarns during twisting or spinning, including spin finishes, lubricants and softening agents, which can be referred to as avivages, can also require water separation or removal. It is, therefore, a further object of the present invention to provide a process which allows relatively pure water to be obtained from a dilute aqueous solution of NMMO, N-methylmorpholine, morpholine or mixtures thereof and from avivages so that the solutions can be concentrated without significant change in the dissolved substances, i.e. the amines contained in the solution.

It is also an object of the invention to provide an improved method of concentrating such amines from dilute aqueous solutions thereof whereby the capital cost of the equipment involved and the operating cost of the equipment involved can be relatively low.

SUMMARY OF THE INVENTION

These objects and others which will become apparent hereinafter are attained in accordance with the invention by a method in which the solution is subjected to reverse osmosis at a pressure greater than the osmotic pressure on a semipermeable membrane. The method of removing water from a dilute aqueous solution of NMMO, N-methylmorpholine, morpholine or a mixture thereof can thus comprise the steps of:

(a) generating a pressure of a dilute aqueous solution of N-methylmorpholine-N-oxide, N-methylmorpholine, morpholine or mixtures thereof in excess of an osmotic pressure of the solution;

(b) subjecting the solution at the pressure in excess of the osmotic pressure to reverse osmosis on a semipermeable membrane to force water as a permeate through the membrane and form a retentate consisting of N-methylmorpholine-N-oxide, N-methylmorpholine, morpholine or mixtures thereof; and (c) separately recovering the permeate and the retentate.

The membrane holds back practically all of the dissolved substances. Especially good results are obtained when the pressure at which the reverse osmosis is carried out is about 40 bar and the temperature between 25° and 75° C.

The water pressed through the membrane is found to be very pure and can be discharged into a sewer system without further treatment or can be recycled to the process as process water. In the latter case, the need for fresh water can be reduced. The amines retained by the membrane form a relatively concentrated retentate since the process of the invention is capable of substantially concentrating these dissolved substances.

It has been found to be advantageous to work up the concentrated solution in any conventional manner to NMMO. This reduces the need for NMMO while avoiding environmental pollution since all of the concentrated amines can be converted to NMMO which can be recycled to the process.

The invention, therefore, provides a process which can completely eliminate the formation of waste water requiring treatment in the production of shaped cellulosic articles using the NMMO solution process. The recirculation of the NMMO and the water greatly improves the economy of the process.

The N-methylmorpholine can be converted to NMMO by oxidation. The morpholine is distilled off from the N-methylmorpholine in a further step. The distilled off morpholine can be methylated to produce N-methylmorpholine which can be oxidized to NMMO. The NMMO is fed back to the process as described.

The formation of NMMO from N-methylmorpholine is described in U.S. Pat. No. 1,144,048, German Democratic Republic Patent 246 997 or German (Federal Republic) Patent 36 18 352 (see also U.S. Pat. No. 4,748,241).

The method of forming N-methylmorpholine from the morpholine can be effected as described in German (Federal Republic) laid open application 32 09 675, German laid open application 37 18 388 or German Patent 35 04 899.

BRIEF DESCRIPTION OF THE DRAWING

The above and other objects, features and advantages of our invention will become more readily apparent from the following description, reference being made to the sole FIGURE of the accompanying drawing of which is a flow diagram of an apparatus for carrying out the method of the present invention.

SPECIFIC DESCRIPTION

A vapor condensate obtained as previously described from the NMMO-cellulose process, in the form of a dilute solution of NMMO, N-methylmorpholine, and morpholine in water, is supplied by a feed pump 1 via a pipe 2 into a circulating or retentate vessel 3.

The liquid in the retentate vessel 3 is fed by a pressure pump 4 which can be a centrifugal pump, through a heat exchanger 5 where the liquid is brought to a predetermined temperature, e.g. the temperature for reverse osmosis of 25° C. to 75° C.

The liquid then flows through a filter 6 and to one or more high pressure pumps 7 which apply to the liquid a pressure sufficient for reverse osmosis and, preferably around 40 bar, corresponding to the reverse osmosis pressure which is higher than the osmotic pressure.

The liquid at this pressure is fed to a membrane module 8 from which practically pure water is removed as the permeate.

The dissolved substances (NMMO, N-methylmorpholine, and morpholine) are held back to form the retentate.

The retentate is fed by line 9 back to the retentate vessel 3. The permeate can be continuously drawn off via line 10 and delivered to the permeate holder 12 which can supply process water to the cellulose dissolution process.

With the aid of the valve V1 downstream of the high pressure pump 7 and the valve V2 downstream of the membrane module 8, the requisite supply and system pressures can be established. The membrane module which can have membrane units connected in series or in parallel, is so selected that it can tolerate the operating temperature and pressure ranges and will have the requisite chemical resistance.

Depending upon the product, the separating effect and the retentate concentration, we can operate the apparatus discontinuously or continuously. In a discontinuous operation, the vapor condensate is passed through the membrane module 8 and returned to the retentate vessel 3. The process is continued until the amine concentration in the retentate vessel 3 reaches the desired final concentration. The retentate is then pumped out for further processing and reuse in the cellulose-dissolving process. Fresh vapor condensate is then added. The valve V3 and line 11 can permit retentate to be continuously withdrawn when the process is operated continuously.

The reverse osmosis technique utilizes a physical characteristic of the molecules which are retained as a basis for the separation. The vapor condensate can be continuously recirculated while amine-free permeate is drawn off so that the concentrate (retentate) recovers by and large all of the solvent which the NMMO process tends to lose, thereby increasing the efficiency of this process. The permeate can be disposed of in a sewer system without contamination problems but is preferably returned as process water to the cellulose dissolving process, thereby saving on expensive fresh water. The separation and concentration of the amines does not require the use of additional chemicals.

By recycling the retentate and use of the permeate instead of fresh water, the solvent recirculation can be completely closed.

Apart from the increase in efficiency and reduction in cost, the invention is characterized by a complete lack of any threat to the environment.

SPECIFIC EXAMPLES

EXAMPLE 1

550 liters of vapor condensate with an amine concentration of 0.07% (molar ratio of N-methylmorpholine to morpholine of 1:1) is fed via the feed pump 1 through the pipe 2 to the retentate vessel 3. The pump 4 feeds this solution via the heat exchanger 5 maintaining a temperature of 30° C. therein through the filter 6 to the high pressure pumps 7 continuously. Using the valves V1 and V2 a reverse osmosis pressure of 40 bar is established in the membrane module 8 for a flow rate of 2.5 m³/h. The membrane module is a coiled membrane of the polysulfone type marketed under the name FILM-TEC SW30 HR4040 (DOW CHEMICALS) with a retention capacity of 99.5% for seawater.

The purified permeate is continuously drawn off by the pipe 10 and the retentate is returned by line 9 to the retentate vessel 3 until the desired concentration is reached, whereupon it is drawn off via the valve V3 for further processing, namely, conversion of morpholine to N-methylmorpholine and the N-methylmorpholine to NMMO.

Every 10 minutes the permeate flow is fixed and samples are taken of the retentate to determine concentration. At the beginning of the separation the permeate flow is 41.1 l/m$^2$/h and the permeate flow decreases during separation to 29.2 l/m$^2$/h. The retentate concentration in the end was 2.1%, i.e. the amines had been concentrated by a factor of 30. The amine concentration in the permeate was between 0.0004% and 0.0011%, corresponding to a retention capacity of the membrane of N-methylmorpholine and morpholine of 99.5 to 99.9% and 98.6 to 99.5% with reference to the starting concentration.

EXAMPLE 2

550 liters of condensate (amine concentration 0.09%) is fed by means of the pump 4 through the heat exchanger 5 which establishes the temperature at 40° C. and through the filter 6 to the high pressure pumps 7. An operating pressure of 40 bar and a flow rate through the membrane of 1.25 l/m$^2$/h is established. The membrane was of the type SW30 HR4040 (DOW CHEMICALS). The purified permeate (amine concentration 0.0009 to 0.042%) is continuously drawn off via line 10. The retentate is recirculated until it has an amine concentration of 10.3%. The amine concentration amounts to 114 times and a separation effect of the membrane of 99% to 99.6% with reference to the retentate concentration. The permeate flow from a starting point of 54.8 l/m$^2$/h and fell with progressive concentration to 5.5 l/m$^2$/h.

EXAMPLE 3

550 liters of vapor condensate (starting concentration of 0.12% amines, ratio of N-methylmorpholine to morpholine of 1:1) is fed by the pump 4 through the heat exchanger 5 maintaining a working temperature of 40° C. to the high pressure pumps 7. The high pressure pumps feed the solution to the membrane module 8 which is equipped with the membrane described in Examples 1 and 2. The flow through the membrane is about 2.5 m$^3$/hour. The operating pressure was 40 bar. By recirculation of the retentate a concentration of 11% is achieved. The continuously withdrawn permeate has an amine concentration of 0.0004% to 0.06%. The retention capacity of the membrane is 99.5% to 99.7% with respect to the retentate concentration. The permeate flow reduces from 57.8 l/m$^2$/h at the inception to 7.5 l/m$^2$/h. The concentration of the amine was a factor of 92.

EXAMPLE 4

The pump 4 feeds 550 liters of a wash water from the last stage of an NMMO process for producing cellulose articles with an NMMO concentration of 0.05% to the heat exchanger which maintains a constant operation temperature of 40° C. The high pressure pumps 7 supply the operating pressure of 40 bar. The concentration of the NMMO is effected on the film membrane of Examples 1 and 2. The flow through the membrane is about 2500 liters per hour and the retentate is recycled to the retentate vessel 3. The permeate is withdrawn continuously and every 15 minutes the permeate flow is determined. The final concentration of the retentate was 6.5%. No NMMO was found in the permeate by an analysis having a limit of detection of 10 ppm. The permeate flow during the separation was between 59.1 l/m$^2$/h and 24.2 l/m$^2$/h. The concentration amounted to 130 times.

EXAMPLE 5

1400 liters of a waste water with a starting concentration of 0.01% NMMO and 0.02% avivage is fed by the pump 4 through the heat exchanger 5 which maintain a temperature of 30° C. to the filter 6 of the high pressure pumps 7. The high pressure pumps develop an operating pressure of 40 bar and reverse osmosis is carried out on a membrane of the types used in Examples 1 and 2 with a flow across the membrane 1.25 m$^3$/h.

The purified permeate is continuously withdrawn via line 10. The retentate is recirculated until its concentration in NMMO reaches 93 g/l. This corresponds to a concentration in NMMO of 930 times. Up to the point at which the NMMO has been concentrated about 600 times, no NMMO could be detected in the permeate. Avivage could not be detected in the permeate even at the highest concentration of the retentate. The retention capacity of the membrane with respect to NMMO was 99.9%. The permeate flow at beginning of the separation was 44.4 l/m$^2$/h and fell with increasing retentate concentration to 4.9 l/m$^2$/h.

We claim:

1. A method of regenerating a spent solvent which is a dilute aqueous solution containing, N-methyl-morpholine, morpholine, or mixtures thereof, to form a fresh solvent for use in a cellulose-dissolving process, said fresh solvent being a mixture of N-methyl-morpholine-N-oxide and water, which comprises the steps of:
    (a) generating a pressure of the dilute aqueous solution containing N-methyl-morpholine, morpholine, or mixtures thereof, in excess of an osmotic pressure of said solution;
    (b) subjecting said dilute aqueous solution at said pressure in excess of said osmotic pressure to reverse osmosis on a semi-permeable membrane to force water as a permeate through said membrane, thereby removing fresh water from said dilute aqueous solution, and forming a retentate comprising N-methyl-morpholine, morpholine and mixtures thereof;
    (c) separately recovering said permeate and said retentate;
    (d) transforming morpholine, N-methyl-morpholine or mixtures thereof in the retentate to N-methyl-morpholine-N-oxide; and
    (e) adding the retentate containing N-methyl-morpholine-N-oxide to the cellulose-dissolving process for reuse thereby regenerating the fresh solvent.

2. The method defined in claim 1 wherein said pressure in excess of the osmotic pressure is substantially 40 bar.

3. The method defined in claim 2 wherein said solution is maintained at a temperature of substantially 25° C. to 75° C. during subjecting of said solution at said pressure in excess of said osmotic pressure to reverse osmosis on said semipermeable membrane.

4. The method defined in claim 1 wherein said solution is maintained at a temperature of substantially 25° C. to 75° C. during subjecting of said solution at said pressure in excess of said osmotic pressure to reverse osmosis on said semipermeable membrane.

* * * * *